United States Patent [19]

Sarges

[11] 4,286,098
[45] Aug. 25, 1981

[54] PROCESS FOR THE PREPARATION OF CHIRAL HYDANTOINS

[75] Inventor: Reinhard Sarges, Mystic, Conn.

[73] Assignee: Pfizer Inc., New York, N.Y.

[21] Appl. No.: 135,137

[22] Filed: Mar. 28, 1980

[51] Int. Cl.³ .......................................... C07D 491/107
[52] U.S. Cl. .................................. 548/309; 260/345.2
[58] Field of Search ................................ 548/309, 308

[56] References Cited

U.S. PATENT DOCUMENTS

| 4,117,230 | 9/1978 | Sarges | 548/309 |
| 4,130,714 | 12/1978 | Sarges | 548/309 |

FOREIGN PATENT DOCUMENTS 217882  5/1957  Australia ................................. 548/308

OTHER PUBLICATIONS

Elderfield, R., (Editor), *Heterocyclic Compounds*, vol. 5, John Wiley, New York, 1957, pp. 258–259.
House, H., Modern Synthetic Reactions, W. A. Benjamin, New York, 1965, p. 11.
Barton, J. in *Protective Groups in Organic Chemistry*, (McOmie, Editor), Plenum Press, London, 1973, pp. 62–63.
March, J., *Advanced Organic Chemistry*, McGraw Hill, New York, 1968, pp. 90–91; 334–335; 346; 667 and 711.
Blank, B. in *Burger's Medicinal Chemistry*, Fourth Ed., (Wolff, Editor), Part II, John Wiley, New York, 1979, pp. 1045–1080.

*Primary Examiner*—Richard A. Schwartz
*Attorney, Agent, or Firm*—Connolly and Hutz

[57] ABSTRACT

A novel process for the synthesis of chiral hydantoins of the structure

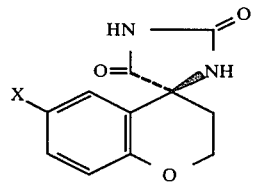
(I)

wherein X is fluoro or chloro, from the corresponding 6-halo-4-chromanone of the structure

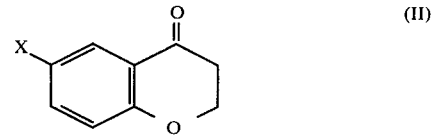
(II)

is described. The compounds I are valuable in the treatment of certain chronic complications arising from diabetes mellitus. In addition the compound of the formula I wherein X is chloro possesses complementary hypoglycemic activity.

The process comprises the sequence of dehydrative coupling of the halochromanone (II) with S-(−)-alpha-methylbenzylamine to form the imine of structure

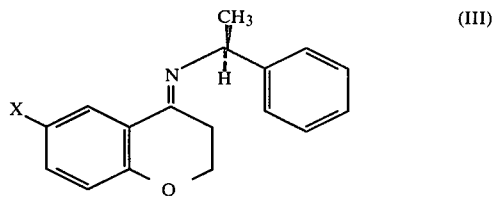
(III)

addition of hydrogen cyanide to form the nitrile of structure

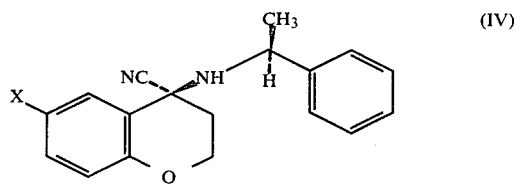
(IV)

condensation with chlorosulfonylisocyanate (or its equivalent) to form the alpha-methylbenzylhydantoin of structure

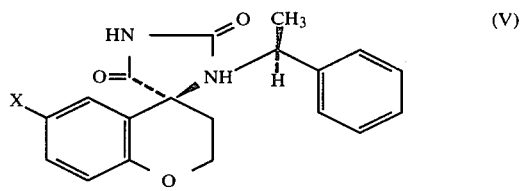
(V)

and finally solvolysis of the latter to the chiral hydantoin of structure I.

4 Claims, No Drawings

PROCESS FOR THE PREPARATION OF CHIRAL HYDANTOINS

BACKGROUND OF THE INVENTION

Racemic (dl or RS) 2,3-Dihyro-6-fluoro-spiro[4H-1-benzopyran-4,4'-imidazolidine]-2',5'-dione and 6-chloro-2,3-dihydro-spiro-[4H-1-benzopyran-4,4'-imidazolidine]-2',5'-dione have heretofore been reported [Sarges, U.S. Pat. No. 4,117,230] to be aldose reductase inhibitors, reflecting their value in controlling certain chronic complications arising from diabetes mellitus (e.g., diabetic cataracts and neuropathy.) Subsequently, in spite of the fact that R-, S- and RS-2,3-dihydro-6-fluoro-spiro-[4H-1-benzopyran-4-4'-imidazoline]-2',5'-dione are equipotent as snticonvulsant agents, it was determined that the aldose reductase activity resided in the S isomer (USAN: sorbinil; the dextrorotatory isomer having structure

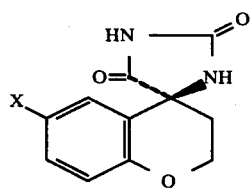

wherein X=F, Sarges U.S. Pat. No. 4,130,714), now a more highly potent aldose reductase inhibitor, reflecting its especial value in effectively controlling the chronic complications of diabetes mellitus.

Sorbinil was heretofore made by the resolution of the racemate, using highly toxic brucine as the resolving agent and wastefully producing an equal amount of the R-isomer which is virtually devoid of the desired activity. Unexpectedly, the resolution process for sorbinil does not provide an enabling disclosure for the synthesis of the corresponding S-6-chloro-2,3-dihydro-spiro-[4H-1-benzopyran-4,4'-imidazolidine]-2',5'-dione.

Also clinically useful in the treatment of diabetes mellitus are insulin and oral hypoglycemic agents such as sulfonylureas (e.g., chlorpropamide, tolbutamide, acetohexamide, tolazamide), biguanides (e.g. phenformin). A variety of other compounds which have been reported to have this type of activity, as recently reviewed by Blank [Burger's Medicinal Chemistry, Fourth Edition, Part II, John Wiley and Sons, N.Y., (1979), pp. 1057–1080].

SUMMARY OF THE INVENTION

The present invention provides an alternative synthesis of sorbinil (I, X=F), avoiding use of highly toxic brucine and further, avoiding wasteful production of less desirable R-isomer. The synthesis, employing 6-fluro-4-chromanone (II, X=F, Sarges, U.S. Pat. Nos. 4,117,230; 4,130,714) is carried out by the following 4-step sequence; wherein X is fluoro:

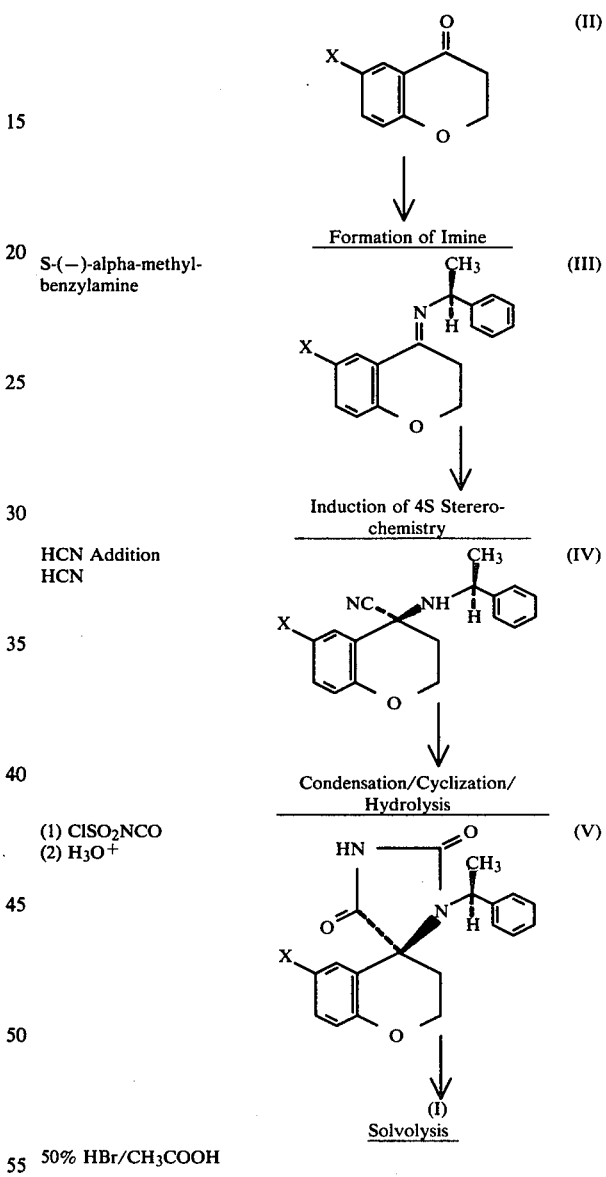

The same synthetic sequence applied to 6-chloro-4-chromanone (II, X=Cl) produces novel and heretofore unavailable S-6-chloro-2,3-dihydro-spiro[4H-1-benzopyran-4,4'-imidazolidine]-2',5'-dione (I, X=Cl). As in the case of the fluoro analog, the desired activity (inhibition of aldose reductase, reflecting control of certain chronic complications arising in diabetes mellitus) resides in the S isomer. However, in spite of the fact that sorbinil lacks hypoglycemic activity, [Peterson et al., Metabolism 28, 456 (1979)], it has been surprisingly found that the chloro analog possesses such hypoglycemic activity. This activity complements the aldose reductase activity of this compound in the treatment of diabetes mellitus and its complications.

DETAILED DESCRIPTION OF THE INVENTION

The novel, four-stage syntheses of sorbinil (X=F) and its novel heretofore unavailable chloro analog (X=Cl) are represented schematically above in the sequence (II)→(III)→(IV)→(V)→(I).

The starting 6-halo-4-chromanones (II, more systematically named as 6-halo-2,3-dihydro-4H-1-benzopyran-4-ones) are available commercially or by literature methods (See Sarges, U.S. Pat. No. 4,117,230).

The initial stage of the synthesis, conversion of II to the imine (III) is usually carried out in an inert, anhydrous solvent, such as an aromatic hydrocarbon (e.g. benzene, toluene) or an ether (tetrahydrofuran, dioxane, 1,2-dimethoxyethane, diglyme). By inert solvent is meant one which will not react significantly with reagents or products under the conditions employed. Selection of a solvent for the reaction is otherwise noncritical. The reaction is preferably carried out under conditions wherein the water is removed from the reaction mixture-either azeotropically (e.g from benzene, toluene or diglyme) or by the addition of a dehydrating agent such as titanium tetrachloride. The latter is the preferred dehydrating agent, since high yields of the desired imine are obtained. The temperature for the reaction is not critical, e.g. from $-10°$ C. to $70°$ C. The middle range of $20°$ C.–$45°$ C. is preferred, since the reaction proceeds at a reasonable rate, being complete in some 6 to 48 hours, with minimal degradation. The reaction is conveniently monitored by infrared spectroscopy: following disappearance of the characteristic ketone carbonyl vibration. In this manner optimal reaction time at any given temperature is readily determined. The molar ratio of ketone, amine and titanium tetrachloride is not critical. It can range from theoretical (1:1:0.5) to 1:4:0.75, with an added base such as a tertiary amine like triethylamine to neutralize the hydrogen chloride produced as a by-product in the reaction or during isolation (e.g. 4 moles of base/mole of titanium tetrachloride. If desired, excess of the amine reactant itself can be used as the base for neutralization of the hydrogen chloride. If reaction is incomplete after the usual reaction time (e.g. in the case where traces of water are inadvertently present), additional titanium tetrachloride can be added to force the reaction to completion.

In the second stage of the 4-stage sequence, hydrogen cyanide is added to the carbon-nitrogen double-bond of the imine (III). It is at this stage that the desired asymmetry at C.4 is induced, through preferential formation and crystallization of the S,S-diastereomer. Anhydrous conditions are employed to prevent possible hydrolysis of of the imine. Selection of a solvent is dictated by the requirement that the desired diastereomer crystallize cleanly therefrom. Ethanol is a solvent well suited for this purpose, but it is evident that simple experimentation would identify other suitable solvents, e.g. other lower alkanols. The temperature of the reaction can be over a range of temperatures, e.g. $-20°$ C. to $35°$ C. Lower temperatures facilitate dissolution of the hydrogen cyanide gas. Intermediate temperatures (e.g. $10°$–$20°$ C.) facilitate crystallization of the product while lower temperatures (e.g. $-5°$ C. to $5°$ C.) improve the yield, since the solubility of the product decreases with temperature. The reaction time is not critical, the range of 0.5 to 6 hours being quite satisfactory. The molar ratio of hydrogen cyanide to imine can range from theoretical 1:1 up to 100:1. Generally, an excess of hydrogen cyanide is employed (e.g. 10:1 to 50:1) in order to improve the reaction rate, forcing it to completion in the specified time.

The third stage in the synthetic sequence is the condensation of the aminonitrile (IV) with chlorosulfonylisocyanate to form the chlorosulfonylurea derivative (VI),

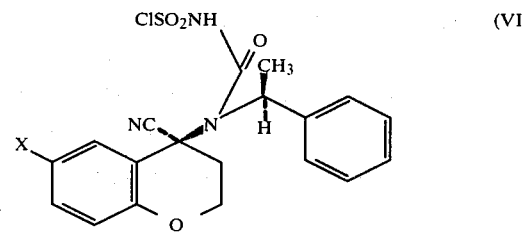

followed by cyclization (with net hydrolysis and elimination of hydrogen chloride and sulfur trioxide) to form the imine (VII), and finally further hydrolysis of the

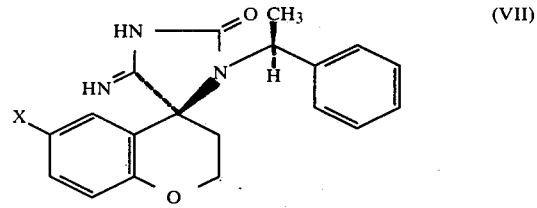

imine to form the phenalkylated hydantoin (V). This sequence represents a novel process for the formation of hydantoins, and is an important feature of the present invention where known hydantoin forming reagents do not perform satisfactorily. The formation of the chlorosulfonylurea (VI) is carried out in an aprotic solvent, inert to the highly reactive chlorosulfonylisocyanate. Suitable solvents are aromatic hydrocarbons (e.g. benzene, toluene), chlorinated hydrocarbons (e.g. methylene chloride, chloroform, chlorobenzene), ethers (e.g. tetrahydrofuran, dimethoxyethane) and the like. The product is usually isolated in crude form by stripping the solvent so that a low boiling solvent such as methylene chloride is particularly well suited for this reaction. The temperature of condensation is not critical (e.g. $0°$–$50°$ C.), but the reaction is so rapid that it is conveniently carried out at room temperature for about 10 minutes. The molar ratio of aminonitrile to chlorosulfonylisocyanate is preferably, but not restricted to, the theoretical 1:1, since clean reaction products result therefrom.

The cyclization to imine (VII), and hydrolysis thereof to the phenalkylated hydantoin is generally carried out without isolation of the imine. These reactions are preferably carried out in hot, aqueous hydrochloric acid, after an initial stirring period of about 10 minutes at ambient temperature. Total reaction time at about $90°$–$105°$ C. is preferably about 2 hours. Since the reaction is heterogeneous, vigorous agitation is helpful in attaining complete conversion of (VI) to (VII) and thence to (V) in the specified reaction time. If desired, the intermediate imine can be isolated. In this case, the reaction is heated immediately following the addition of aqueous hydrochloric acid, conditions which happen to be conducive to the precipitation of the intermediate imine hydrochloride. When the imine precipitates, a longer reaction time, with the addition of more aqueous acid if desired, will complete conversion of the imine to the hydantoin (V). Alternatively, the isolated imine can be converted to the hydantoin (V) by heating in additional aqueous hydrochloric acid.

The fourth and final stage of the syntheses of the present invention is solvolysis of the phenalkylated hydantoins (V) to the desired, aldose reductase inhibiting hydantoins (I). Although the alpha-methylbenzyl group can be removed by a variety of acid conditions, the preferred method is to carry out the hydrolysis by heating the substituted hydantoin in a mixture of strong, aqueous hydrobromic acid (e.g 48%) and acetic acid. The reaction is conveniently monitored by standard thin layer chromatographic techniques, permitting facile determination of optimal temperature and reaction times. A temperature of about 105° C. to 145° C. is generally preferred, with reaction times of 1 to 6 hours, depending upon the temperature.

The aldose reductase inhibitory activity of S-6-chloro-2,3-dihydro-spiro[4H-1-benzopyran-4,4'-imidazolidine]-2',5'-dione (I, X=Cl) was determined in vitro by measuring the inhibition of isolated aldose reductase from human placenta, a test similar to the calf lens enzyme test of Peterson et al. [Metabolism 28, 456 (1979)]. As in the case of sorbinil (I, X=F), high activity rests in the S-enantiomer [Sarges, U.S. Pat. No. 4,130,714; Peterson et al, loc. cit.].

The surprising hypoglycemic activity of S-6-chloro-2,3-dihydro-spiro[4H-1-benzopyran-4,4'-imidazolidine]-2',5'-dione (I, X=Cl), was determined by the test procedure which follows. Intact male albino rats, each weighing approximately 150–200 grams are the experimental test animals employed for such purposes. The test animals are fasted approximately 18–24 hours. The rats are weighed, numbered, and recorded in groups of five or six as needed. Each animal is then dosed intraperitoneally with glucose (one gram per kilogram) and orally with either water (controls) or compound (20 mg./kg.). Blood glucose levels (mg./100 ml.) are measured in tail blood samples over a period of 3 hours in both control and treated groups. The results obtained with the chloro compound (I, X=Cl) were as follows:

|  | Blood Glucose levels (mg/100 ml) | | | | |
| --- | --- | --- | --- | --- | --- |
|  | 0 hr. | 0.5 hr. | 1 hr. | 2 hr. | 3 hr. |
| Control | 64 | 128 | 111 | 81 | 74 |
| Compound (I, X=Cl) | 72 | 113 | 102 | 76 | 72 |

It will be particularly noted that in the control group the glucose level (mg./100 ml.) increased by 100% at the 0.5 hr. time point, whereas in the test group, blood glucose level increased by only 57% over the 0 time level. This result is surprising, in view the fact that sorbinil (I, X=F), lacks this type of activity [Peterson et al., loc. cit.], a fact reconfirmed by more recent test results:

|  | Blood Glucose levels (mg/100 ml) | | | | |
| --- | --- | --- | --- | --- | --- |
|  | 0 hr. | 0.5 hr. | 1 hr. | 2 hr. | 3 Hr. |
| Control | 53 | 101 | 98 | 73 | 68 |
| Compound (I, X=F) | 56 | 104 | 93 | 69 | 69 |

The hypoglycemic activity of the S-chloro compound is even more surprising in view of the fact that the earlier racemic chloro compound of U.S. Pat. No. 4,117,230 shows no such activity, as illustrated by the following test results:

|  | Blood Glucose levels (mg/100 mg) | | | | |
| --- | --- | --- | --- | --- | --- |
|  | 0 hr. | 0.5 hr. | 1 hr. | 2 hr. | 3 hr. |
| Control | 71 | 128 | 120 | 100 | 91 |
| Racemic Chloro Compound | 65 | 121 | 116 | 91 | 87 |

Since in the disease state of diabetes mellitus it is desirable to reduce blood glucose levels, as well as to control chronic complications which arise therefrom, the two types of biological activity found in the S-chloro compound are complementary, adding a special and novel dimension to the utility of this compound. Thus the S-6-chloro-2,3-dihydro-spiro-[4H-1-benzopyran-4,4'-imidazoline-2',5'-dione of the present invention is administered to a diabetic subject at a level and in a manner set forth for sorbinil in U.S. Pat. No. 4,130,714. As well as controlling chronic complications of diabetes, the chloro analog functions as a hypoglycemic agent, reducing the level of (or even eliminating the need for) coadministered hypoglycemic agents.

The present invention is illustrated by the following examples. However, it should be understood that the invention is not limited to the specific details of these examples.

EXAMPLE 1

S-2,3-Dihydro-6-fluoro-4-(1-phenylethylimino)-4H-1-benzopyran (III, X=F).

A flame dried 3 neck flask fitted with a mechanical stirrer, dropping funnel, $N_2$ inlet, and thermometer was charged with 0.83 g (5 mmoles) of 2,3-dihydro-6-fluoro-4H-1-benzopyran-4-one (Sarges, U.S. Pat. Nos. 4,117,230; 4,130,174) and 30 ml of dry benzene. The solution was cooled to 0° and to it was added a solution of 1.94 ml. (15 mmoles) of S-(−)-alpha-methylbenzylamine in 15 ml of dry benzene. After 15 minutes and while keeping the temperature below 10°, a solution of 0.275 ml. (2.5 mmoles) of $TiCl_4$ in 10 ml of benzene was added dropwise over 20 min. The red-brown suspension was allowed to warm to room temperature and stirred for 18 hours. At this time, another 0.5 ml. of S-(−)-alpha-methylbenzylamine was added, followed after 15 minutes by another 0.1 ml. of $TiCl_4$ in 5 ml of benzene. After stirring for an additional 3hours at room temperature, i.r. analysis of a filtered aliquot showed no ketone carbonyl and a new strong band at 1635 $cm^{-1}$. The suspension was filtered through a coarse sintered glass funnel charged with celite and the filter cake was washed twice with 50 ml. portions of benzene. The filtrate was concentrated in vacuo to a tacky residue, which was triturated several times with petroleum ether. The combined triturates were filtered and the filtrate concentrated in vacuo to yield 1.07 g. (80%) of S-2,3-dihydro-6-fluoro-4-(1-phenylethylimino)-4H-1-benzopyran (oil; i.r. 1650 $cm^{-1}$; m/e 269).

EXAMPLE 2

S-6-Chloro-2,3-dihydro-4-(1-phenylethylimino)-4H-1-benzopyran (III, X=Cl)

By the same procedure as Example 1, 5 g (0.027 mol) of 6-chloro-2,3-dihydro-4H-1-benzopyran-4-one, 10.6 ml (0.082 mol) of S-(−)-alpha-methylbenzylamine, and 1.5 ml (0.0137 mole) of titanium tetrachloride in 275 ml of dry benzene gave, after a 24 hour reaction time without the addition of more reagents, 7.1 g (91%) of S-6-chloro-2,3-dihydro-4-(1-phenylethylimino)-4H-1-benzopyran [viscous oil; m/e 287/285; nmr ($CDCl_3$-TMS) delta 1.5 (d, 3H); 2.7 (t,2H), 4.2 (t,2H), 5.75 (q,1H); 6.8 (d,1H); 7.1–7.5 (m,6H); 8.2 (d,1H)].

EXAMPLE 3

S-4-Cyano-2,3-dihydro-6-fluoro-4-(S-1-phenylethylamino)-4H-1-benzopyran (IV, X=F)

A hydrogen cyanide generator (a 3 neck flask containing 15 ml. of 50% aqueous sulfuric acid, fitted with a dropping funnel containing an aqueous solution of 6.8 g. of sodium cyanide in 30 ml. of water) was connected by tubing via a calcium chloride drying tube to the inlet tube of the main reaction vessel, a 3-necked round bottom flask with a magnetic stirrer and a perfusion capillary tube which could be lowered below the solvent surface. Throughout the reaction a gentle stream of nitrogen was passed through the hydrogen cyanide generator, the reaction flask, and finally through a neutralizing trap containing 5 N sodium hydroxide. The reaction flask was charged with S-2,3-dihydro-6-fluoro-(1-phenylethylimino)-4H-1-benzopyran (2.7 g., 10 mmoles) in 60 ml. of absolute ethanol and cooled to −10° C. Hydrogen cyanide was generated over about 30 minutes by adding the sodium cyanide solution dropwise to the sulfuric acid. The hydrogen cyanide generator was warmed, and all remaining hydrogen cyanide flushed into the reactor with nitrogen (about 45 minutes). The reaction mixture was warmed to room temperature. Filtration gave 2.105 g. (71%) of S-4-cyano-2,3-dihydro-6-fluoro-4-(S-1-phenylethylamino)-4H-1-benzopyran [m.p. 130°–132° C. (dec.)].

Anal. Calcd. for $C_{18}H_{17}N_2OF$: C, 72.95; H, 5.78, N, 9.46. Found: C, 73.01, H, 5.88, N, 9.45.

EXAMPLE 4

S-6-chloro-4-cyano-2,3-dihydro-4-(S-1-phenylethylamino)-4-H-1-benzopyran (IV, X=Cl)

Using the procedure of Example 3, 1.01 g. (3.53 mmol) of S-6-chloro-2,3-dihydro-4-(1-phenylethylimino)-4H-benzopyran in 15 ml of ethanol was reacted with hydrogen cyanide made from 1.73 g. (35.3 mmol) of sodium cyanide in 8 ml. of water and 4 ml. of 50% sulfuric acid. The hydrogen cyanide was generated over 10 minutes. Residual hydrogen cyanide was flushed into the reaction mixture by heating the generator to 80° C. for 5 minutes. The reaction mixture was warmed to 0° C. and filtered to yield 781 mg (71%) of S-6-chloro-4-cyano-2,3-dihydro-4-(S-1-phenylethylamino)-4H-1-benzopyran [mp 146°–8° C. (dec.)].

Anal. Calcd. for $C_{18}H_{17}ClN_2O$: C, 69.11, H, 5.48; N, 8.96. Found: C, 69.36; H, 5.62; N, 9.05.

EXAMPLE 5

S-2,3-Dihydro-fluoro-3'-(S-1-phenylethyl)-spiro[4H-1-benzopyran-4,4'-imidazolidine]-2',5'-dione (V, X=F)

To a solution of 0.25 g. (0.84 mmoles) of S-4-cyano-2,3-dihydro-6-fluoro-4-(S-1-phenylethylamino)-4H-1-benzopyran in 10 ml. of methylene chloride was added 48 mg. (0.34 mmol) of chlorosulfonyl isocyanate. After stirring 10 minutes at room temperature, the solution was concentrated in vacuo to a foam. After addition of 7.5 ml. of 1 N hydrochloric acid the suspension was stirred for 10 minutes at room temperature, followed by heating on a steam bath for 1 hour. After cooling to room temperature, the precipitated solid was filtered, washed with water, and dried to give 168 mg. (50%) S-2,3-dihydro-6-fluoro-3'-(S-1-phenylethyl)-spiro[4H-1-benzopyran-4,4'-imidazolidine]-2',5'-dione (mp 226°–8°). An analytical sample was prepared by recrystallization from ethanol-water.

Anal. Calcd. for $C_{19}H_{17}FN_2O_3$: C, 67.05, H, 5.04, N, 8.23. Found: C, 66.79, H, 5.18, N, 8.38.

By reheating the filtrate, a second crop (10–20%) is obtained. Alternatively, by heating the reaction on a steambath for 2 hours, after addition of the hydrochloric acid, yields of about 79% are obtained directly, without need to obtain second crop by further heating of the filtrate.

EXAMPLE 6

S-6-Chloro-2,3-dihydro-3'-(S-1-phenylethyl)-spiro[4H-1-benzopyran-4,4'-imdazolidine]-2',5'dione (V,X=Cl)

By the procedure of Example 5, 0.5 g. (1.6 mmol) of S-6-chloro-4-cyano-2,3-dihydro-4-(S-1-phenylethylamino)-4H-1-benzopyran and 0.14 ml (1.6 mmol) of chlorosulfonyl isocyanate gave 0.509 g. (89%) of S-6-chloro-2,3-dihydro-3'-(S-1-phenylethyl)-spiro[4H-1-benzopyran-4,4'-imidazolidine]-2',5'-dione [mp 268°–70° C.].

Anal. Calcd. for $C_{19}H_{17}ClN_2O_3$: C, 63.95, H, 4.80, N, 7.85. Found: C, 63.66, H, 4.98, N, 7.67.

EXAMPLE 7

S-2,3-Dihydro-6-fluoro-spiro[4H-1-benzopyran-4,4'-imidazolidine]2',5'-dione (Sorbinil; I, X=F)

To a suspension of 0.23 g. (0.68 mmol) of S-2,3-dihydro-6-fluoro-3'-(S-1-phenylethyl)-spiro[4H-1-benzopyran-4,4'-imidazolidine]2',5'-dione in 8 ml of glacial acetic acid was added 15 ml of 48% hydrobromic acid. After heating 2 hours at 120°–30° C. (oil bath temperature), tlc (ethyl acetate-hexane 1:1; visualization with phosphomolybate spray/charring) showed two new spots (product, Rf 0.45; alpha-bromoethylbenzene, Rf 0.95) in addition to starting material (Rf 0.75). After cooling the reaction mixture, the solvents were removed in vacuo to give a liquid which was dissolved in 50 ml of ethyl acetate, washed twice with water, dried over with anhydrous magnesium sulfate, filtered, and evaporated to an oil. This oil was triturated with methylene chloride to give 80 mg. (50%) of sorbinil [m.p. 238°–239.5° (reference mp 241°–3°; Sarges, U.S. Pat. No. 4,130,714), $[alpha]_D^{25} = +53.1°$ (c=1, MeOH; reference rotation $[alpha]_D^{25} = +54°$ loc. cit.)].

EXAMPLE 8

S-6-chloro-2,3-dihydro-spiro[4H-1-benzopyran-4,4'-imidazolidine]-2',5'-dione (I, X=Cl)

By the method of Example 7, 100 mg. (0.2 mmol) of S-6-chloro-2,3-dihydro-3'-(S-1-phenylethyl)-spiro[4H-1-benzopyran-4,4'-imidazolidine]-2',5'-dione was converted to 38 mg (54%) of S-6-chloro-2,3-dihydro-spiro[4H-1-benzopyran-4,4'-imidazolidine]-2',5'-dione as the monohydrate [mp 244°-6°; [alpha]$_D^{25}$= +46.6° (c=1, MeOH)]

Anal. Calcd. for $C_{11}H_9ClN_2O_3 \cdot H_2O$: C, 48.80, H, 4.09, N, 10.35. Found: C, 49.14, H, 3.69, N, 10.13.

EXAMPLE 9

S-2,3-Dihydro-6-fluoro-5'-imino-3'-(S-1-phenylethyl)-spiro[4H-1-benzopyran-4,4'-imidazolidine]-2'-one, (VII, X=F)

The intermediate imine of Example 5 was isolated as follows.   S-4-cyano-2,3-dihydro-6-fluoro-4-(S-1-phenylethylamino)-4H-1-benzopyran 1.5 g. (5 mmoles) and chlorosulfonylisocyanate (0.44 ml., 5 moles) in 25 ml of methylene chloride was stirred at room temperature for 20 minutes, and the solvent removed in vacuo to give a pale yellow foam. To this material was added 45 ml of 1 N hydrochloric acid; and the suspension was heated immediately for 1.5 hours on a steam bath, then cooled to room temperature and filtered to give 1.67 g. of a pale yellow solid. The latter material was chromatographed on 60 g. of 230-400 mesh silica gel, eluting with methylene chloride to give 0.4 g. of S-2,3-dihydro-6-fluoro-3'-(S-1-phenylethyl)-spiro[4H-1-benzopyran-4,4'-imidazolidine]-2',5'-dione, 0.04 g of sorbinil, and 0.965 g. of S-2,3-dihydro-6-fluoro-5'-imino-3'-(S-1-phenylethyl)-spiro-[4H-1-benzopyran-4,4'-imidazolidine[2'-one as a white solid (mp 73°-5° dec).

Anal. Calcd. for $C_{19}H_{18}FN_3O_2 \cdot 2HCl$: C, 55.35, H, 4.89, N, 10.19. Found: C, 55.65, H, 4.50, N, 9.91.

Heating this product and 2 ml of 1 N HCl on a steam bath for 30 minutes gave, after cooling and filtering, S-2,3-dihydro-3'-(S-1-phenylethyl)-spiro[4H-1-benzopyran-4,4'-imidazolidine]-2',5'-dione.

I claim:

1. The process for preparing a chiral hydantoin of the formula

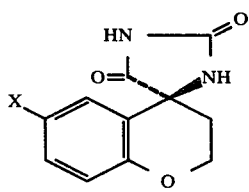

(I)

wherein X is chloro or fluoro, from the corresponding halochromanone of the formula

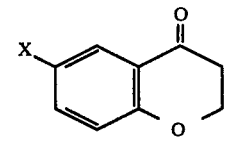

(II)

which comprises the sequence of dehydrative coupling of the chromanone with S-(−)-alpha-methylbenzylamine to form the imine of the formula

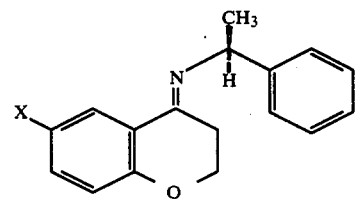

(III)

adding the elements of hydrogen cyanide to the imine in an anhydrous organic solvent to selectively form and crystallize the chiral nitrile of the formula

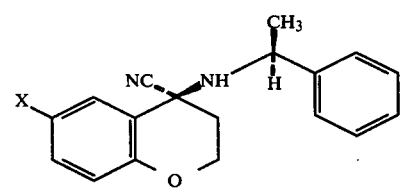

(IV)

condensing the nitrile with chlorosulphonyl isocyanate in a reaction-inert solvent, followed by cyclization and hydrolysis in aqueous acid to form the alpha-methylbenzylhydantoin of the formula

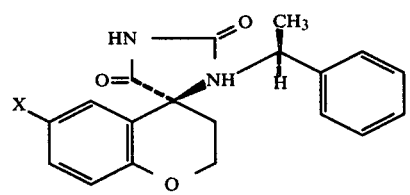

(V)

and solvolyzing the alpha-methylbenzylhydantoin in a strong acid to the chiral hydantoin of formula I.

2. A process of claim 1 wherein X is fluoro.
3. A process of claim 1 wherein X is chloro.
4. The compound of the formula

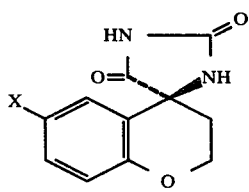

(I)

wherein X is chloro.

* * * * *